(12) United States Patent  (10) Patent No.: US 8,709,359 B2
Laugharn, Jr.  (45) Date of Patent: Apr. 29, 2014

(54) SAMPLE HOLDER AND METHOD FOR TREATING SAMPLE MATERIAL

(75) Inventor: James A. Laugharn, Jr., Winchester, MA (US)

(73) Assignee: Covaris, Inc., Woburn, MA (US)

( * ) Notice: Subject to any disclaimer, the term of this patent is extended or adjusted under 35 U.S.C. 154(b) by 452 days.

(21) Appl. No.: 12/984,919

(22) Filed: Jan. 5, 2011

(65) Prior Publication Data

US 2012/0167786 A1 Jul. 5, 2012

(51) Int. Cl.
*G01N 1/28* (2006.01)
*G02B 21/34* (2006.01)
*B01L 3/00* (2006.01)

(52) U.S. Cl.
USPC ............... 422/536; 422/554; 422/559

(58) Field of Classification Search
USPC ........... 422/50, 430, 500, 536, 527, 547, 551, 422/552, 554, 559, 560, 561; 435/307.1, 435/283.1; 73/864.91, 863
See application file for complete search history.

(56) References Cited

U.S. PATENT DOCUMENTS

| | | | |
|---|---|---|---|
| 1,734,975 A | 11/1929 | Loomis et al. | |
| 2,447,061 A | 8/1948 | Franklin | |
| 2,565,159 A | 8/1951 | Williams | |
| 2,578,505 A | 12/1951 | Benson | |
| 2,585,103 A | 2/1952 | Fitzgerald | |
| 2,632,634 A | 3/1953 | Williams | |
| 2,738,172 A | 3/1956 | Spiess, Jr. et al. | |
| 2,855,526 A | 10/1958 | Jones | |
| 2,864,592 A | 12/1958 | Camp | |
| 2,916,265 A | 12/1959 | Towne | |
| 2,950,725 A | 8/1960 | Jacke et al. | |
| 3,066,686 A | 12/1962 | O'Neill | |
| 3,194,640 A | 7/1965 | Nesh | |
| 3,292,910 A | 12/1966 | Martner | |
| 3,379,315 A * | 4/1968 | Broadwin | 211/72 |
| 3,396,286 A | 8/1968 | Anderson et al. | |
| 3,481,186 A | 12/1969 | Plofsk | |
| 3,604,270 A | 9/1971 | Falk | |

(Continued)

FOREIGN PATENT DOCUMENTS

DE 738286 8/1943
EP 0707892 5/1996

(Continued)

OTHER PUBLICATIONS

Invitation to Pay Additional Fees and Partial International Search for International Patent Application PCT/US2012/020149 dated Apr. 3, 2012.

(Continued)

*Primary Examiner* — Christopher A Hixson
(74) *Attorney, Agent, or Firm* — Wolf, Greenfield & Sacks, P.C.

(57) ABSTRACT

Method and apparatus for holding and/or treating a sample material. A sample material may be positioned in a vessel between top and bottom flexible films where the flexible films are connected together by a substantially rigid support structure that surrounds the sample material. A crushing force may be applied to the sample material via the top and bottom flexible films, e.g., to pulverize the sample at cryogenic temperatures. A sample holder may have two vessels, one arranged for applying a crushing force to a first sample and another for holding a sample for other processing, such as a histology analysis.

32 Claims, 4 Drawing Sheets

(56) References Cited

U.S. PATENT DOCUMENTS

| | | |
|---|---|---|
| 3,614,069 A | 10/1971 | Murry |
| 3,743,523 A | 7/1973 | Bodine |
| 3,807,704 A | 4/1974 | Janzen et al. |
| 3,837,805 A | 9/1974 | Boucher |
| 3,876,890 A | 4/1975 | Brown et al. |
| 3,919,558 A | 11/1975 | Brouillette et al. |
| 4,028,933 A | 6/1977 | Lemons et al. |
| 4,307,964 A | 12/1981 | Dudgeon et al. |
| RE31,779 E | 12/1984 | Alliger |
| 4,488,816 A | 12/1984 | Vota |
| 4,541,281 A | 9/1985 | Chubachi et al. |
| 4,571,087 A | 2/1986 | Ranney |
| 4,644,808 A | 2/1987 | Lecoffre |
| 4,764,905 A | 8/1988 | Granz et al. |
| 4,834,124 A | 5/1989 | Honda |
| 4,862,060 A | 8/1989 | Scott et al. |
| 4,879,011 A | 11/1989 | Schram |
| 4,889,122 A | 12/1989 | Watmough et al. |
| 4,926,871 A | 5/1990 | Ganguly et al. |
| 4,983,189 A | 1/1991 | Peterson et al. |
| 5,026,167 A | 6/1991 | Berliner, III |
| 5,037,481 A | 8/1991 | Bran |
| 5,224,658 A | 7/1993 | Smith |
| 5,368,054 A | 11/1994 | Koretsky et al. |
| 5,395,592 A | 3/1995 | Bolleman et al. |
| 5,409,594 A | 4/1995 | Al-Jiboory et al. |
| 5,484,573 A | 1/1996 | Berger et al. |
| 5,523,058 A | 6/1996 | Umemura et al. |
| 5,586,732 A | 12/1996 | Yamauchi et al. |
| 5,601,526 A | 2/1997 | Chapelon et al. |
| 5,612,218 A | 3/1997 | Busch et al. |
| 5,623,095 A | 4/1997 | Beller |
| 5,631,425 A | 5/1997 | Wang et al. |
| 5,639,423 A | 6/1997 | Northrup et al. |
| 5,681,396 A | 10/1997 | Madanshetty |
| 5,688,406 A | 11/1997 | Dickinson et al. |
| 5,736,100 A | 4/1998 | Miyake et al. |
| 5,759,162 A | 6/1998 | Oppelt et al. |
| 5,779,985 A | 7/1998 | Sucholeiki |
| 5,803,099 A | 9/1998 | Sakuta et al. |
| 5,831,166 A | 11/1998 | Kozuka et al. |
| 5,834,648 A | 11/1998 | Wang et al. |
| 5,890,802 A | 4/1999 | Evensen et al. |
| 5,962,338 A | 10/1999 | Sucholeiki |
| 5,993,671 A | 11/1999 | Peltzer |
| 6,003,388 A | 12/1999 | Oeftering |
| 6,010,316 A | 1/2000 | Haller et al. |
| 6,039,309 A | 3/2000 | Kuklinski |
| 6,042,556 A | 3/2000 | Beach et al. |
| 6,086,821 A | 7/2000 | Lee |
| 6,100,084 A | 8/2000 | Miles et al. |
| 6,210,128 B1 | 4/2001 | Rife et al. |
| 6,224,778 B1 | 5/2001 | Peltzer |
| 6,244,738 B1 | 6/2001 | Yasuda et al. |
| 6,277,332 B1 | 8/2001 | Sucholeiki |
| 6,284,113 B1 | 9/2001 | Bjornson et al. |
| 6,291,180 B1 | 9/2001 | Chu |
| 6,361,747 B1 | 3/2002 | Dion et al. |
| 6,413,783 B1 | 7/2002 | Wohlstadter et al. |
| 6,440,725 B1 | 8/2002 | Pourahmadi et al. |
| 6,515,030 B1 | 2/2003 | Bechtel et al. |
| 6,699,711 B1 | 3/2004 | Hahn et al. |
| 6,719,449 B1 | 4/2004 | Laugharn, Jr. et al. |
| 6,737,021 B2 | 5/2004 | Watari et al. |
| 6,948,843 B2 | 9/2005 | Laugharn, Jr. et al. |
| 7,211,927 B2 | 5/2007 | Puskas |
| 7,328,628 B2 | 2/2008 | Laugharn, Jr. et al. |
| 7,329,039 B2 | 2/2008 | Laugharn, Jr. et al. |
| 7,560,074 B2 | 7/2009 | Yamamoto et al. |
| 7,677,120 B2 | 3/2010 | Laugharn, Jr. et al. |
| 2002/0187547 A1* | 12/2002 | Taylor et al. ............... 435/306.1 |
| 2003/0066915 A1 | 4/2003 | Taylor |
| 2003/0165482 A1 | 9/2003 | Rolland et al. |
| 2004/0054286 A1 | 3/2004 | Audain et al. |
| 2004/0076545 A1 | 4/2004 | Watari et al. |
| 2004/0264293 A1 | 12/2004 | Laugharn et al. |
| 2005/0142664 A1 | 6/2005 | Loney |
| 2005/0150830 A1 | 7/2005 | Laugharn et al. |
| 2005/0235740 A1 | 10/2005 | Desie et al. |
| 2006/0029525 A1 | 2/2006 | Laugharn et al. |
| 2006/0158956 A1 | 7/2006 | Laugharn et al. |
| 2007/0053795 A1 | 3/2007 | Laugharn et al. |
| 2007/0069054 A1 | 3/2007 | Shomi |
| 2007/0218455 A1 | 9/2007 | Knize et al. |
| 2008/0031094 A1 | 2/2008 | Laugharn et al. |
| 2008/0050289 A1 | 2/2008 | Laugharn et al. |
| 2008/0056960 A1 | 3/2008 | Laugharn et al. |
| 2009/0084202 A1 | 4/2009 | Mimori et al. |
| 2010/0243773 A1 | 9/2010 | Cope et al. |

FOREIGN PATENT DOCUMENTS

| | | |
|---|---|---|
| EP | 0709136 | 5/1996 |
| SU | 1462155 | 2/1989 |
| WO | WO 9502456 | 1/1995 |
| WO | WO 0025125 | 5/2000 |
| WO | WO 02088296 A1 | 11/2002 |
| WO | WO 2005056748 A1 | 6/2005 |
| WO | WO 200701660 | 2/2007 |

OTHER PUBLICATIONS

International Search Report and Written Opinion from International Patent Application PCT/US2004/040133 dated Apr. 20, 2005.

International Search Report and the Written Opinion of the International Searching Authority for PCT Application No. PCT/US2012/020149, Dated Jul. 3, 2012.

* cited by examiner

SAMPLE HOLDER AND METHOD FOR TREATING SAMPLE MATERIAL

BACKGROUND

A first step in sample analysis typically involves collecting the sample. For example, a first step in a biological analysis such as RNA gene expression profiling or protein biomarker profiling is to collect a particular sample so that its biochemical constituents can be analyzed. However, prior to such analysis, a solid sample specimen, typically, is prepared by deconstructing it into a plurality of smaller fragments of the specimen to enable more accurate analysis.

A challenge of sample preparation is that the types of samples are diverse. For example, samples may be biological, non-biological or a combination thereof. They may be from animals or plants. Samples may include, without limitation, cells, tissues, organelles, bones, seeds, chemical compounds, minerals, metals, or any other material for which analysis is desired.

Sample preparation is particularly challenging for solid biological samples, such as tissue samples. Physical and/or chemical approaches are often employed to disrupt and homogenize the solid sample for biochemical extraction. While appearing deceptively simple, transitioning a sample of biologically active tissue, for example, on the order of 1 gram, to a plurality of biomolecules that are stabilized and isolated in an appropriate analytical solution is exceedingly complex, very difficult to control, and prone to introduction of errors and/or sample constituent degradation.

Another challenge associated with sample preparation relates to the lability of the target molecules. For some applications, an overriding criterion is to retain the native biochemical environment prior to sample collection and throughout the extraction process, without perturbing the biochemical constituents to be analyzed. For example, RNases are extremely robust and may significantly degrade the mRNA profile of a tissue sample if the RNases are not immediately stabilized (typically thermal or chemical inactivation) at the time of tissue collection and during sample processing or homogenization. Often, to minimize perturbation of the biochemical profile of the sample, the tissue is flash-frozen (e.g., via direct immersion of the sample following procurement in liquid nitrogen) and stored at cryogenic temperatures (e.g., −80 degrees C. or lower), which inhibits degradative processes.

SUMMARY OF INVENTION

Aspects of the invention address at least some of these challenges by providing, in various embodiments, systems, methods and devices for collecting, stabilizing, fragmenting and/or analyzing samples. As described above, analysis of biological and non-biological sample specimens often begins with collection of a sample of relatively large size. Before the constituents of such a sample can be effectively analyzed, the sample, preferably, is fragmented into a plurality of smaller specimens. Such smaller specimens can then be stored, analyzed, or further processed. In one embodiment, a sample holder includes two vessels arranged so that one portion of a sample may be placed into a first vessel and another portion of the same sample may be placed into a second vessel. The first vessel may be arranged to allow the sample to be frozen (e.g., by exposure to liquid nitrogen or other suitable cryogen) and then fragmented, broken, or otherwise crushed without removing the sample from the first vessel. The second vessel may be arranged to store the sample under conditions suitable for later histologic or other analysis of the sample. Thus, the two sample portions may be kept together on a common support, e.g., so that if analysis results of one sample portion require the use of the other sample portion for other tests or confirmation of the first analysis, one can be assured that the sample portions originated from the same subject and have been stored under the same or similar conditions.

A sample may be any material. Exemplary samples include, but are not limited to, bones, teeth, seeds, plants, pathological or non-pathological animal tissue (e.g., muscle, liver, kidney, lung, brain, pancreas, prostate, ovary, breast, etc.), tumor tissue, rocks, mineral samples, tree bark, and/or food products. Exemplary constituents include, but are not limited to, nucleic acids, amino acids, polypeptides, bacteria, viruses, fungi, spores, small organic molecules, small inorganic molecules, metals, minerals, ores, and the like. The sample may be relatively soft, such as a tissue sample, may be relatively hard, such as a bone or mineral sample, and may include sharp knife-like edges and/or sharp needle-like points. By way of a more particular example of the medical application of the invention, it may be used to process pathological and/or non-pathological tissue samples harvested from a patient. Such samples include, but are not limited to, putative tumor samples taking during a biopsy.

In one aspect of the invention, a sample holder includes a support structure defining first and second vessels, with each of the vessels including a top opening, e.g., into which a sample portion may be placed. First and second covers may be each removably engageable with the support structure so as the close the top opening of the first and second vessels, respectively. For example, the covers may be in the form of a cap that is arranged to seal a corresponding vessel closed and be openable to allow retrieval of all or part of a sample portion from the vessel. The first vessel may be arranged to contain a first sample material and transmit a crushing force exerted on the first vessel to the first sample material so as to crush the first sample material. For example, the vessel may be placed in a device arranged to apply a crushing impact force to the first vessel and first sample material, e.g., as described in U.S. Patent Publication US 2005/0132775 which is hereby incorporated by reference in its entirety. The second vessel may be arranged to contain a second sample material suitable for a desired analysis process, such as a histology analysis.

A sample holder arranged like that described above may provide advantages such as allowing a sample harvester (such as a doctor taking a biopsy sample) to place one portion of a sample in the first vessel and another portion of the same sample in a second vessel. The two sample portions may be stored together, experiencing the same, or similar, conditions. In addition, by harvesting and placing the sample in the vessels at the same time, there may be confidence that the samples originated from the same source, were taken using the same or similar techniques, and so on. Accordingly, if analysis of a first sample portion (e.g., resulting from the first sample material in the first vessel being crushed and subsequently subjected to a molecular analysis to identify whether a particular compound is present) suggests that further or different analysis is required, the second sample portion in uncrushed or other form may be used (e.g., as part of a histology analysis). In some embodiments, the second vessel may be separable from the first vessel, e.g., the second vessel may be used as a histology cassette.

In another illustrative embodiment, a sample holder may include a support structure defining a substantially rigid sidewall of a vessel, a bottom opening of the vessel, and a top opening of the vessel. A first layer of flexible film may be attached to the support structure so that the first layer of film covers the bottom opening, and a second layer of flexible film may be attached to the support structure so that the second layer covers the top opening. The first and second layers may be separated from each other by at least a part of the sidewall and be arranged to transmit a crushing force exerted on the first and second layers to crush a sample material contained in the vessel, e.g., between the first and second layers and within the sidewall. By having the flexible films separated from each other by a substantially rigid sidewall, the sample material in the vessel may be crushed, yet the vessel may retain at least some of its initial shape and/or size. This is in contrast to bag-type sample holders that are commonly used for sample crushing. While these bag-type sample holders are very effective, retrieval of a crushed sample may require that the bag be manipulated to separate the bag layers from each other and/or move the sample to a desired location in the bag. Sample holders in accordance with some embodiments may allow for crushing of the sample while maintaining the sample in a relatively defined space that can be easily accessed.

The sample holder may be arranged for use with a variety of analysis tools, such as microscopes and other imaging devices, impact devices, microtome devices, acoustic treatment devices, and so on. For example, the sample holder support structure may define a generally planar body in which the sidewall is defined and/or from which the sidewall extends, e.g., the support structure may define a shape similar or identical to a microscope slide and the sidewall may extend upwardly from the planar body and/or have a cylindrical shape. Films on top and bottom sides of the planar body may close top and bottom openings defined by the support structure, and thereby define a vessel in which a sample material is held. In one embodiment, a sample contained in the vessel may be held by the vessel for viewing in a microscope or other imaging system either before or after the sample is crushed while in the vessel.

In some embodiments, the first and/or second layers of flexible film may have a convex shape such that a portion of the first and/or second layer extends into the vessel, or the first and/or second layer may have a concave shape such that a portion of the first and/or second layer extends away from the vessel. The concave and/or convex shapes may provide certain features, such as providing a well or other area in which a sample is held, may help hold a sample in place in the vessel (e.g., by squeezing the sample in place between the two layers), may help direct a sample or portions of the sample to specific areas in the vessel, and so on. The first and/or second layers may be formed of a polyimide, a polysulfone, a fluorinated polymer, a liquid crystal polymer or other suitable material. For example, the first and second layers may be arranged to transmit the crushing force to the sample material while at temperatures less than about −40 degrees C., e.g., after the vessel and sample are immersed in liquid nitrogen or are otherwise exposed to cryogenic conditions. The first and second layers may transmit the crushing force to the sample material at such low temperatures without cracking, tearing, or ripping when exposed to the crushing force. This can be a useful property, particularly if the sample is relatively hard, e.g., includes a seed, bone, rock, stone, sand, glass, metal, tree bark, and fragments and combinations thereof, and/or when the crushing force transmits significant energy to the sample, e.g., of at least up to about 10 Joules or more. The first and second layers may have any suitable thickness, e.g., of between about 0.5 mil and 5 mil.

In one illustrative embodiment, a sample holder may include a support structure that defines a sidewall of a vessel having a bottom opening and a top opening. A first layer of flexible film may be attached to the support structure to cover the bottom opening, and a cap may be removably engageable with the support structure so as the close the top opening of the vessel. The cap may include a cap opening and a second layer of flexible film may cover the cap opening. The first and second layers of film may be arranged to transmit a crushing force exerted on the first and second layers to crush a sample material contained in the vessel. The vessel may be sealed in a substantially air tight fashion when the cap is engaged with the support structure, e.g., to isolate a sample in the vessel from an external environment. The top and bottom openings may have any suitable size and/or shape, such as a circular opening with a diameter of about 20 mm. The first and/or second layers may be substantially flat or have a concave or convex shape, e.g., a convex portion that extends into the vessel and has an outer diameter of about 5 mm and a height of about 2 mm.

In another aspect of the invention, a method of treating a sample material includes providing a sample material between top and bottom flexible films where the flexible films are connected together by a substantially rigid structure that surrounds the sample material, and applying a crushing force to the sample material via the top and bottom flexible films. The first and second films and the structure may be arranged like that described above, e.g., in an arrangement that defines a cylindrically-shaped space in which the sample is held and a crushing force is exerted from opposite ends of the cylindrically-shaped space.

In another aspect of the invention, a method for treating a sample material includes providing first and second portions of a sample material. The first and second portions may be obtained from a single piece of the sample material, e.g., the first and second portions may be cut from a single biopsy sample or other piece of material. The first portion of the sample material may be contained in a first vessel, and a second portion of the sample material may be contained in a second vessel, where the first and second vessels are attached together. The first and second vessels may be arranged to suitably isolate the sample material from an exterior environment, e.g., to help prevent contamination and/or degradation of the sample material. The first portion of the sample material may be crushed while the first portion is contained in the first vessel, and the second portion may be stored in the second vessel for a histology analysis of the second portion of the sample material. In one embodiment, the first portion may be crushed while the first and second vessels are attached together, e.g., as part of a single, multiple vessel sample holder. Crushing may take place while the sample material is at a relatively low temperature, such as below −40 degrees C. A molecular analysis of first portion may be performed after crushing, e.g., to analyze whether the first portion includes one or more compounds. Depending on the outcome of the molecular analysis, a histology analysis of second portion may be performed. For example, if the molecular analysis of the first portion indicates the possible presence of a particular tissue morphology or other characteristic, the histology analysis may be performed to identify whether the morphology or other characteristic is present.

These and other aspects of the invention will be apparent from the following description and claims.

BRIEF DESCRIPTION OF THE DRAWINGS

Aspects of the invention are described with reference to illustrative embodiments shown in the drawings, in which like numerals reference like elements, and wherein.

DETAILED DESCRIPTION

It should be understood that illustrative embodiments are described in accordance with aspects of the invention. However, the embodiments described are not necessarily intended to show or incorporate all aspects of the invention, but rather are used to describe a few illustrative embodiments. Thus, aspects discussed herein are not intended to be construed narrowly in view of the illustrative embodiments. In addition, it should be understood that aspects of the invention described may be used alone or in any suitable combination with other aspects also described.

Figure 1:
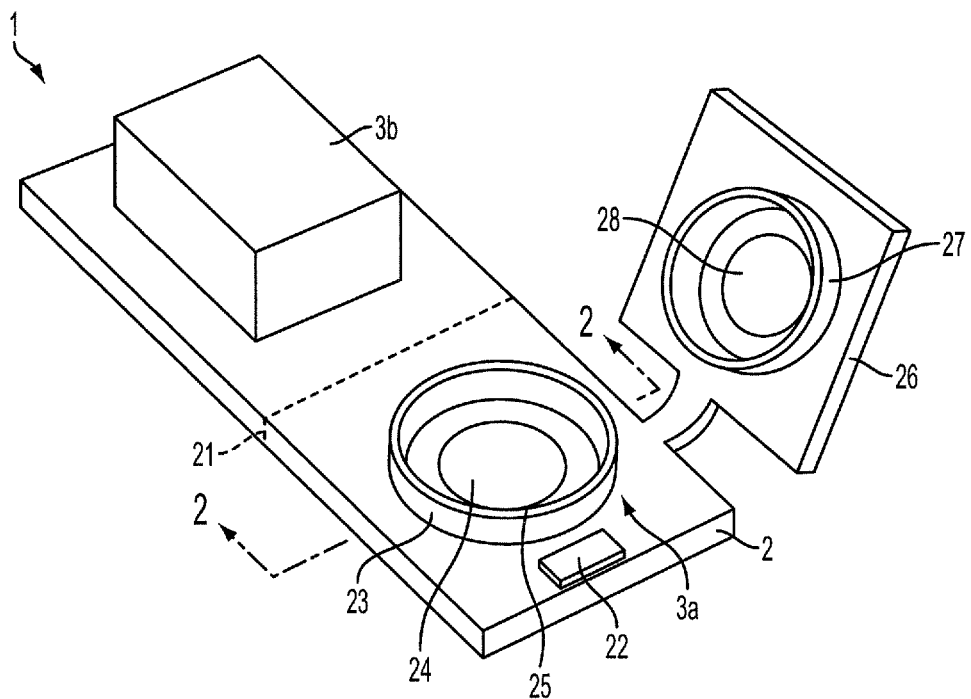
FIG. 1 shows a perspective view of a sample holder having two vessels in an illustrative embodiment.

FIG. 1 shows a perspective view of an illustrative embodiment of a sample holder 1 that incorporates one or more aspects of the invention. In this embodiment, the sample holder 1 includes a support structure 2 that is made of a polymer material (such as polycarbonate, polyethylene, polypropylene, polyimide, PTFE, etc.) and has the overall size and shape of a conventional microscope slide. However, it should be understood that the support structure 2 may have any size, shape or other configuration, and may be made of any suitable material, including glass, metal, composites, etc. The sample holder 1 includes two vessels 3 including a first vessel 3a and a second vessel 3b, but may include only one vessel or three or more vessels. The vessels 3 are configured differently in this embodiment, with the first vessel 3a being arranged to hold a sample material for crushing (discussed in more detail below), while the second vessel 3b is arranged to hold a sample material for use in a histology analysis (e.g., the second vessel 3b may have the form of a standard histology cassette). However, the vessels 3, if two or more are provided, may be arranged in the same or similar way, or may be arranged to hold samples for other purposes. For example, sample material may be stored for any suitable length of time and in a variety of different conditions based on the particular sample, its intended use, etc. Exemplary storage periods include short term storage for minutes (e.g., less than or equal to 30 minutes) or hours (e.g., less than or equal to 1 to 12 hours). Further exemplary storage periods include overnight storage or storage for 1 or more days, weeks, months, or years.

In accordance with an aspect of the invention, the vessels 3 are separable from each other, e.g., by hand and without the use of tools. For example, in this embodiment, the support structure 2 includes a line of weakness 21, such as a perforation, disengagable snaps or other fasteners, or other feature that allows the vessels 3 to be separated from each other. Such a feature may be useful, for example, for harvesting the samples placed in the vessels at the same time and from the same subject while ensuring that the samples travel together for at least some portion of the analysis process. At some point in the process, the samples may be separated by separating the vessels 3 from each other to permit the samples to be subjected to different analysis procedures. An identifier 22, such as a barcode, RFID tag, alphanumeric text, a security feature (e.g., that interacts with an impacting machine to enable crushing of the sample and/or provides information to the machine for proper adjustment of a crushing force, impact energy, impact speed, or other crushing parameter) or other feature that allows the sample holder 1 to be identified and/or be associated with the samples held in the vessels 3, may be provided. The identifier 22 may be used in a variety of different ways, e.g., to track the movement of the sample holder 1, to associate information regarding a sample held by the vessels 3 with the sample holder 1 in a database, and so on. If the sample holder 1 has separable vessels 3 or other portions, the same or different identifiers 22 may be provided for the separable portions.

In this illustrative embodiment, the support structure 2 defines a sidewall 23 of the vessel 3a. The vessel 3a has a bottom opening 24 and a top opening 25 through which a sample material may be placed into the vessel 3a. Although in this embodiment, the sidewall 23 has a generally cylindrical or circular shape, the sidewall 23 may have any suitable shape, such as conical, elliptical, square or other rectangular, triangular, or other shape. In addition, although the sidewall 23 in this embodiment is defined by a hole in the planar body of the support structure as well as an upstanding portion on the planar body, the sidewall 23 may be formed by any suitable structure(s). The top opening 25 may be closed by a cap or other cover 26 to ensure the sample material is kept in the vessel 3a. The cover 26 may engage with the support structure 2 to provide a fluid-tight and/or air-tight seal, e.g., to help isolate the sample material from an exterior environment. This feature may be useful to help ensure that the sample material does not degrade and/or is not contaminated after harvesting. In this embodiment, the cover 26 includes a lip 27 that engages with the sidewall 23 in a snap fit, interference fit, friction fit, or other suitable engagement. The cover 26 and/or the support structure 2 may include one or more seal elements, such as a silicon O-ring seal, a lubricant, a threaded engagement or other arrangement to help form a suitable engagement of the cover 26 with the support structure. Although in this embodiment the cover 26 engages the support structure 2 with a snap-fit, the cover 26 may engage in other ways, such as by a screw thread, a clamp, clip or other fastener. The cover 26 may also include a cover opening 28, which may be generally aligned with the bottom opening 24 when the cover 26 is engaged with the support structure 2.

In accordance with an aspect of the invention, both the bottom opening 24 and the top opening 25 may be closed by a flexible film or layer that is arranged to transmit a crushing force to a sample material in the vessel 3a. For example, a first layer of film may be attached to support structure 2 to close the bottom opening 24 and a second layer of film may be attached to the cover 26 to close the cover opening 28. Accordingly, when the cover 26 is engaged with the support structure 2 to close the vessel 3a, the second layer of film and the cover 26 may close the top opening 25 of the vessel 3a.

Figure 2:
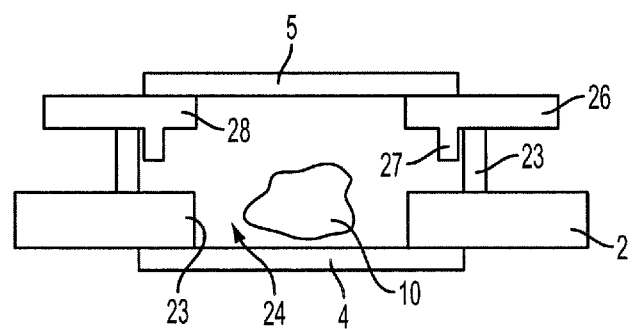
FIG. 2 shows a cross sectional view along the line 2-2 of FIG. 1.

FIG. 2 shows a cross sectional view of the vessel 3a along the line 2-2 as shown in FIG. 1. Unlike that in FIG. 1, in this view, the cover 26 is engaged with the support structure 2 so as to close the top opening 25 of the vessel 3a. In this embodiment, a first layer of film 4 is attached to the support structure 2 so as to close the bottom opening 24. Similarly, the second layer of film 5 is attached to the support structure 2 by way of the cover 26 to close the cover opening 28.

That is, the second layer 5 may be bonded to the cover 26 and be attached to the support structure 2 when cover is engaged with the support structure 2. The first and second layers 4 and 5 may be attached in any suitable way, such as by adhesive, thermal bonding, mechanical clamps or other fasteners, and so on. Thus, the attachment of the layers 4, 5 may be permanent (e.g., not intended for removal) or removable (e.g., by releasing a cover or a clamp, clip, or other fastener). With the first and second layers 4, 5 closing the bottom and top openings 24, 25 of the vessel 3a, the sample material 10 is trapped in a space bounded by the sidewall 23 and the first and second films 4, 5.

Figure 3:
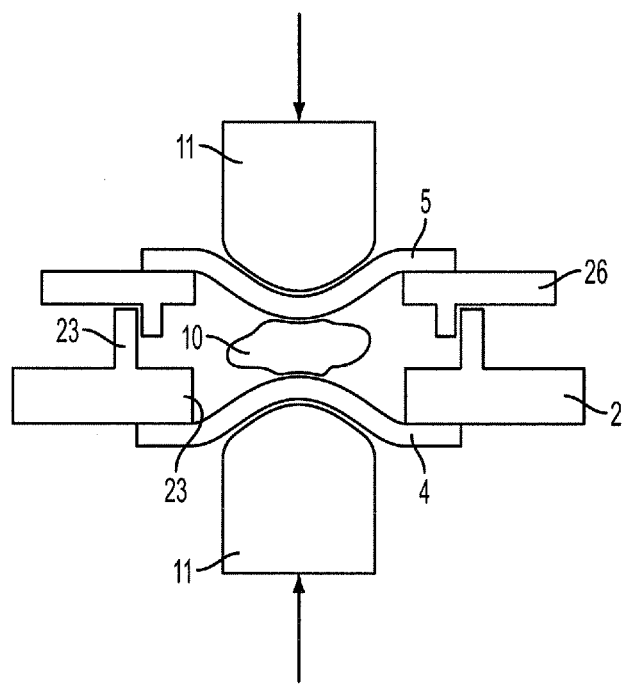
FIG. 3 shows a cross sectional view of the FIG. 1 embodiment while a crushing force is applied to the sample material in the vessel.

The first and second films 4, 5 and the support structure 2 may be arranged to allow the sample material 10 to be crushed while held in the vessel 3a. For example, as shown in FIG. 3, the sample material 10 may be impacted by a pair of impact elements 11 that are sized and configured to apply a crushing force to the sample material 10 by contacting the first and second films 4, 5. Thus, the sample material 10 may be crushed without necessarily causing damage to the first and second films 4, 5 and/or the support structure 2. As a result, the sample material 10 may be crushed, e.g., in preparation for molecular analysis, while maintaining the sample material 10 in a sealed environment. Deflection of the first and second films 4, 5 may vary depending on the application, and in some cases the films 4, 5 may deflect up to 1 mm or more where the sample material has a mass of about 50 milligrams or less. Of course, those of skill in the art will appreciate that the films 4, 5 may deflect to greater extents, such as up to 10 mm or more, and the sample material may have a larger mass, such as up to 250 milligrams or more.

In some embodiments, the films 4, 5 are flexible enough to deform nondestructively (e.g., without experiencing cracking, tearing, ripping or other degradation in structural integrity), or substantially nondestructively, in response to a mechanical impact sufficient to fragment the sample material 10 contained within the sample vessel 3. According to one feature, subsequent to the mechanical impact, the sample holder 1 may maintain sufficient structural integrity to continue to separate the sample material 1 from the external environment. For example, the vessel may maintain the sample in sterile isolation from the external environment. According to various implementations, the mechanical impact may have an impact energy transfer of about 1 to 25 Joules or more. In addition, the crushing force may be applied with the sample material 10 and/or the vessel 3 at cryogenic temperatures below about −20 degrees C. to about −80 degrees C. or less (such as about −196 degrees C.). Of course, in some embodiments, the sample holder 1 may be arranged for use only at non-cryogenic temperatures, such as room temperature and/or temperatures above the freezing point of water.

Depending at least in part on the mechanical properties of the sample material 10 (e.g., relatively hard, relatively soft, forms sharp or pointed shards when fragmented, etc.) and the temperature at which fragmentation is to occur, various materials may be used for the sample holder 1. For example, a brain sample may require a particular film layer thickness (e.g., 1 mil layer of Kapton). Alternatively, a bone, seed, or rock sample, which may have sharp and or pointed features, may require a thicker film layer thickness (e.g., 4 mil layer of Kapton). Also, an additional reinforcement layer, for example, of a non-woven polymer material, such as Tyvek (™) (available from Dupont), reinforcement by woven or non-woven material, or other suitable reinforcement may be provided for the films 4, 5. In the example of FIGS. 2 and 3, the films 4, 5 are formed as separate members (e.g., pieces of sheet material) that are attached to the support structure 2, but in other configurations, the sample holder 1 may be entirely, or include portions that are, injection molded as a single, unitary part. For example, the entire sample holder 10 may be molded of a polyimide material, with various portions, including the sidewall 23 and films 4, 5 molded as a single part, yet having a thickness and/or other structural arrangement to function as desired. In various embodiments, the sample holder 1 may include, at least in part, a polyimide, polysulfone, liquid crystal polymer, fluorinated polymer, and/or other like material, e.g., as part of the films 4, 5.

In various embodiments, the sample holder 10 may be sized and shaped for insertion into, and functional interoperation with, a mechanical impact device, such as that described in U.S. Patent Publication US 2005/0132775. For example, the impact elements 11 may include metal members that are driven together by a hammer, an electromagnetically-driven solenoid piston, a pneumatically-actuated device, a hydraulically-actuated device, a gravity actuated device, or any other suitable mechanism. Also, one of the impact elements 11 may remain stationary while only one element 11 moves toward the other rather than having both elements 11 move. Although the impact device may operate a cryogenic temperatures, the impact providing device may also operate at or about room temperature while still applying a crushing force when the sample material 10 is at cryogenic temperatures. That is, even though the impact device may be at room temperature, the impact device may operate quickly enough so that the transient exposure of the sample holder 1 to the impact elements 11 does not substantially warm the sample material 10. This is also the case where the sample material 10, itself, is maintained at room or near room temperature. In various embodiments, the impact device may provide elements for heating or cooling the sample prior or subsequent to fragmenting it. For example, one or both of the impact elements 11 may be chilled (e.g., by liquid nitrogen), and contact of the sample holder 1 with one or both of the impact elements 11 may chill the sample material 10. The mechanical impact from the impact elements 11 may provide a force sufficient to disrupt the macro-structure of the sample material 10, and fragment it into a plurality of pieces in the vessel 3. Illustratively, the impact force may be between about 1 Joule and about 25 Joules. The impact elements 11 may impact the vessel 3 one or more times to achieve the desired sample fragmentation. For example, the vessel 3 and sample material 10 may be contacted 1 to 5, or more times, and each impact may have the same or different force or impact energy applied. For example, the impact force may be initially larger to break a large sample into fragments, and then be reduced.

In some embodiments, the sample holder 1 may also be arranged for use with other types of sample preparation devices than an impact device. For example, the sample holder 1 may be arranged for use with an acoustic treatment device, such as that described in U.S. Pat. No. 6,948,843. Thus, the sample holder 1 may be used to provide focused acoustic energy to the sample contained within the vessel for performing any one of: cooling; heating; fluidizing; mixing; stirring, disrupting, increasing permeability of a component of, enhancing a reaction of, sterilizing; and/or further fragmenting the sample material.

Figure 4:
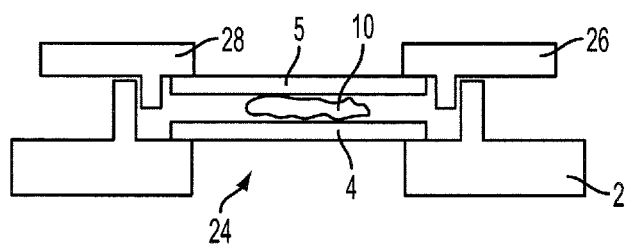
FIG. 4 shows a cross sectional view of a vessel in another illustrative embodiment.
Figure 5:
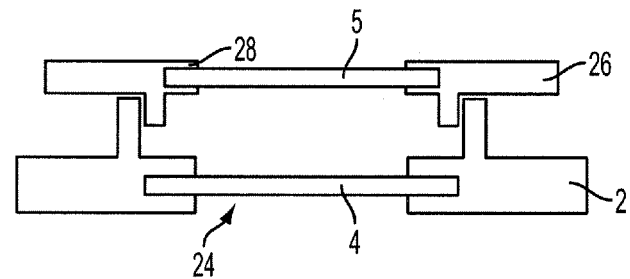
FIG. 5 shows a cross sectional view of a vessel in another illustrative embodiment in which the first and second layers are molded with a support structure and cap.

FIGS. 1-3 show only one illustrative embodiment, and a sample holder that incorporates one or more aspects of the invention may be arranged in other ways. For example, FIG. 4 shows a cross sectional view of an embodiment that is arranged like that in FIG. 1, with a difference being that the first film 4 is attached to the support structure 2 above the bottom surface of the support structure 2 to close the bottom opening 24. In addition, the second film 5 is attached to the cover 26 below the cover's upper surface to close the cover opening 28. As with other embodiments, the first and second films 4, 5 may be molded integrally with the support structure 2 and/or a cover 26, or arranged in other suitable ways. FIG. 5 shows another illustrative embodiment in which the first and second films 4, 5 are attached to the support structure 2 and the cover 26 at a location that is intermediate that shown in FIGS. 2 and 4. With the arrangement shown in FIG. 5, the films 4, 5 may be clamped by portions of the supporting structure 2 or the cover 26, or the support structure 2 and/or cover 26 may be molded to surround the edges of the films 4, 5 (e.g., pieces of suitable sheet material for the films 4, 5 may be provided into an injection mold, and the supporting structure 2 and cover 26 co-molded to envelop the edges of the sheet material).

Figure 6:
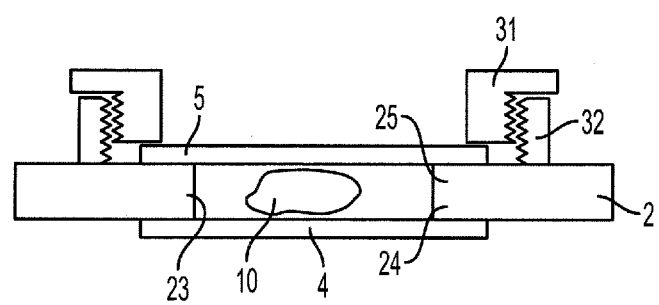
FIG. 6 shows a cross sectional view of a vessel in another illustrative embodiment including a cap that is threadedly engaged with a support structure.

As discussed above, the films 4, 5 may be clamped in place so as to attach the films 4, 5 to the support structure 2 and/or the cover 26 (if provided). For example, FIG. 6 shows an illustrative embodiment in which the first film 4 is attached to a bottom surface of a support structure 2 to close a bottom opening 24 defined by a sidewall 23, and a second film 5 is attached to a top surface of the support structure 2 to close a top opening 25 defined by the sidewall 23 (e.g., where the sidewall 23 is defined by a hole in the support structure 2). While in this embodiment the first film 4 is permanently bonded to the support structure 2, e.g., by thermal welding, adhesive, etc., the second film 4 may be clamped in place and be removable from the support structure 2. While the clamping arrangement may be configured in a variety of different ways, in this embodiment the clamp includes a ring 31 (which may also be referred to as a cover 26) that has a threaded portion that engages with a threaded portion of the supporting structure 2. By threadedly engaging the ring 31 to the support structure 2, the ring 31 may squeeze the second film 5 between the ring 31 and the support structure 2, attaching the second film 5 to the support structure 2. Of course, the second film 5 may be bonded to the lower surface of the ring 31, if desired, rather than be separate from the ring 31.

Figure 7:
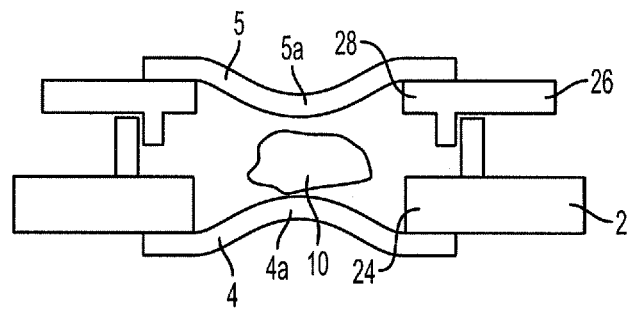
FIG. 7 shows a cross sectional view of a vessel in another illustrative embodiment in which the first and second layers have a convex feature.

In another aspect of the invention, the first and/or second films 4, 5 may be arranged to help position the sample material 10 as desired in the vessel 3. For example, FIG. 7 shows an arrangement that is like that in FIG. 2, except that the first and second films 4, 5 each have a convex portion 4a, 5a that extends into the vessel 3a. The convex portions 4a, 5a are present in the films 4, 5 without an external force being applied to the films 4, 5 (e.g., are molded into the films 4, 5) and may be arranged so as to clamp or otherwise squeeze the sample material 10 between the films 4, 5, thereby helping to hold the sample material 10 in place. Thus, once the cover 26 is engaged with the support structure 2 (or the vessel 3 is otherwise closed), the sample material 10 may be held as desired in the vessel, e.g., for later impact processing. The convex portions 4a, 5a may be molded or otherwise formed into the films 4, 5, and may be compliant to a desired extent. In one embodiment, the convex portions 4a, 5a may have a dome-like shape with a largest diameter of about 5 mm and a height of about 2 mm. In this embodiment, the bottom opening 24 and cover opening 28 may have a diameter of about 20 mm. Of course, it should be understood that other dimensions and shapes other than circularly-shaped openings and convex portions are possible. For example, the openings and convex portions may have an elliptical shape, square shape, and others. It should also be understood that only one of the films 4, 5 may have a convex portion, while the other film may be substantially flat or have other arrangements.

Figure 8:
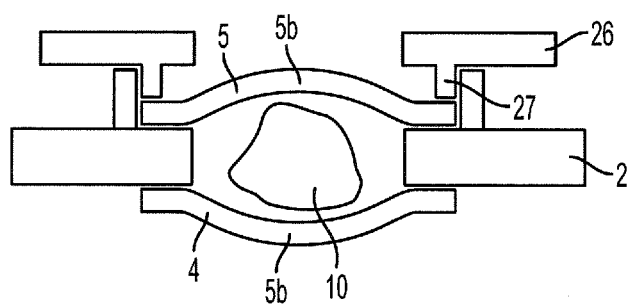
FIG. 8 shows a cross sectional view of a vessel in another illustrative embodiment in which the first and second layers have a concave feature.

For example, FIG. 8 shows an embodiment in which the first and second films 4, 5 each have a concave portion 4b, 5b that extends away from the vessel 3. Another difference in this embodiment as compared to that in FIG. 2 is that the second film 5 is attached to a bottom surface of the lip 27 of the cover 26. As discussed above, the cover 26 may engage the support structure 2 in any suitable way, such as by interference fit, threaded engagement, clamp, etc. In this embodiment, engagement of the cover 26 with the support structure 2 may also serve to clamp the second film 5 to a surface of the support structure 2, although this arrangement is not necessary.

A concave feature 4b, 5b provided with the films 4, 5 may also help position a sample material 10 as desired in a vessel 3. For example, a concave feature 4b on the first film 4 may provide a depression or well into which the sample material 10 may be placed. Thus, the sample material 10 may naturally move to a center of the vessel 3, e.g., by the force of gravity. Although in this embodiment, the second film 5 also has a concave feature, the second film 5 could include a convex feature like that in FIG. 8 which may be used to provide a biasing force on the sample material 10 to keep the sample material 10 in the center of the concave portion 4b of the first film 4.

After suitable treatment of the sample material 10 in the vessel 3, such as freezing, crushing, acoustic treatment to further break the material into smaller particles, etc., the vessel 3 may be opened and the sample material 10 transferred to another sample holder 1. In one embodiment, the sample holder 1 may be arranged to sealingly couple with another sample holder, such as a tube, to help ease transfer of the sample material 10. For example, the vessel 3a in FIG. 1 may opened by lifting the cover 26 and a tube engaged with the sidewall 23 of the support structure 2. Then, the support structure 2 and vessel 3a may be inverted, causing the sample material 10 to be transferred into the tube.

Embodiments in accordance with the invention may be arranged to accommodate an increase in air or other gas pressure in the vessel 3 during crushing of the sample material 10. That is, when the sample material 10 is impacted in some embodiments, the volume of the vessel 3 may be decreased, if only momentarily, increasing the gas pressure in the vessel 3. To compensate, and while maintaining a sealed environment for the sample material, the vessel 3 may be arranged to "burp", i.e., to release gas through a one-way valve, through a seal between the cover 26 and support structure 2 or other pathway when the sample is impacted. While gas may be released from the vessel 3, the sample holder 1 may be arranged to prevent the inflow of gas into the vessel 3, thus maintaining the sample material isolated from an external environment. In other embodiments, the films 4, 5 and/or other portions of the sample holder 1 may be arranged to accommodate an increase in gas pressure. For example, portions of the films 4, 5 that are not contacted by the impact elements 11 or other similar structures during crushing may move to accommodate gas in the vessel 3 so as to maintain the same pressure or another elevated pressure that does not compromise a seal of the vessel 3. In one embodiment, one or both films 4, 5 may include a convex portion in areas not contacted by the impact elements 11 that move (e.g., from a convex configuration to a concave configuration) to accommodate an increase in gas pressure. Other arrangements are possible, such as a gas reservoir, a pressure release valve, etc.

Other aspects of the invention relate to methods for processing sample material. In one aspect, a method for treating a sample material includes providing a sample material between top and bottom flexible films where the flexible films are connected together by a substantially rigid support structure that surrounds the sample material, and applying a crushing force to the sample material via the top and bottom flexible films. As discussed above, by having the films connected together by a substantially rigid structure that is interposed between the films and surrounds the sample material, the sample material may be contained in a relatively defined area that is easily accessed. The flexible films may include suitable features, such as a concave or convex shape that contacts the sample material. Such features may be useful to help locate the sample material for crushing and/or removal. The crushing force may be applied while the sample material is at a temperature less than about −40 degrees C. and without cracking, tearing, or ripping the top and bottom flexible films.

In another aspect of the invention, a method for treating a sample material includes providing first and second portions of a sample material, where a first portion of the sample material is contained in a first vessel, and a second portion of the sample material is contained in a second vessel. The first and second vessels may be attached together, e.g., by a line of weakness or other feature that allows the vessels to be separated from each other by hand and without tools. The first portion of the sample material may be crushed while the first portion is contained in the first vessel, and the second portion may be stored in the second vessel for a histology analysis of the second portion of the sample material.

In some embodiments, crushing of the first sample may be performed while the first and second vessels are attached together, e.g., while the first sample is at cryogenic temperatures. Crushing of the sample may prepare it for a molecular analysis, such as testing to discover the presence of one or more compounds in the sample. Depending on the outcome of the molecular analysis, a histology analysis of the second portion may be performed.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only. It will be apparent that other embodiments and various modifications may be made to the present invention without departing from the scope thereof. The foregoing description of the invention is intended merely to be illustrative and not restrictive thereof. The scope of the present invention is defined by the appended claims and equivalents thereto.

The invention claimed is:

1. A sample holder comprising:
a support structure defining a substantially rigid sidewall of a vessel, the support structure defining a bottom opening and a top opening,
a first layer of flexible film attached to the support structure, the first layer of film covering the bottom opening;
a second layer of flexible film attached to the support structure, the second layer covering the top opening; and
a cap removably engagable with the support structure so as the close the top opening of the vessel, wherein the cap is arranged to sealing engage the second layer with the support structure to cover the top opening,
wherein the first and second layers of film are separated from each other by the sidewall and are arranged to transmit a crushing force exerted on the first and second layers to crush a sample material contained in the vessel.

2. The holder of claim 1, wherein at least a portion of the sidewall extends from a generally planar body of the support structure.

3. The holder of claim 2, wherein the sidewall has a cylindrical shape and extends upwardly from the generally planar body.

4. The holder of claim 1, wherein the support structure defines sidewalls for two separate vessels.

5. The holder of claim 1, wherein the first and/or second layer have a convex shape such that a portion of the first and/or second layer extends into the vessel.

6. The holder of claim 1, wherein the first and/or second layer have a concave shape such that a portion of the first and/or second layer extends away from the vessel.

7. The holder of claim 1, wherein the first and/or second layer is formed of a polyimide, a polysulfone, a fluorinated polymer or a liquid crystal polymer.

8. The holder of claim 1, wherein the first and second layers are arranged to transmit the crushing force to the sample material while at temperatures less than about −40 degrees C.

9. The holder of claim 1, wherein the first and second layers are arranged to transmit the crushing force to the sample material at temperatures less than about −40 degrees C. without cracking, tearing, or ripping when exposed to the crushing force.

10. The holder of claim 1, wherein the first and second layers are arranged to transmit the crushing force to the sample material where the crushing force transfers energy to the sample material of at least about 10 Joules.

11. The holder of claim 1, wherein the first and second layers have a thickness of between about 0.0005 and 0.0005 inches.

12. The holder of claim 1, wherein the vessel is sealed in a substantially air tight fashion with the first and second layers covering the bottom and top openings, respectively.

13. The holder of claim 1, wherein the top and bottom openings have a size of about 20 mm.

14. The holder of claim 1, wherein the first layer includes a convex portion that extends into the vessel and has a dome shape with an outer diameter of about 5 mm and a height of about 2 mm.

15. The holder of claim 1, wherein the support structure is arranged for use as a standard microscope slide.

16. The holder of claim 1, wherein the sidewall has a height of about 2 mm to about 10 mm.

17. The holder of claim 1, wherein the support structure defines a second vessel arranged to hold a sample suitable for microtome processing.

18. A sample holder comprising:
a support structure defining first and second vessels, each of the vessels including a top opening,
first and second covers that are each removably engagable with the support structure so as to close the top opening of the first and second vessels, respectively; and
wherein the first vessel is arranged to contain a first sample material and transmit a crushing force exerted on the first vessel to the first sample material to crush the first sample material,
wherein the first vessel includes a bottom opening opposite the top opening, the sample holder further comprising:
a first layer of flexible film attached to the support structure, the first layer of film cover the bottom opening of the first vessel; and
a second layer of flexible attached to the support structure, the second layer covering the top opening of the first vessel, wherein the first and second layers of film are separated from each other by a portion of the support structure and are arranged to transmit a crushing force exerted on the first and second layers to crush a sample material contained in the vessel, and wherein the second vessel is arranged to contain a second sample material suitable for a histology analysis.

19. The sample holder of claim 18, wherein the first and second vessels are separable from each other without the use of tools.

20. The sample holder of claim 18, wherein the first cover includes a cover opening, and the second layer of flexible film is attached to the cover to close the cover opening, and wherein the second layer of flexible film covers the top opening of the first vessel with the first cover engaged with the support structure.

21. The sample holder of claim 18, wherein the first and second layers are arranged to transmit the crushing force to the sample material at temperatures less than about −40 degrees C. without cracking, tearing, or ripping when exposed to the crushing force.

22. The sample holder of claim 18, wherein the first and second layers are arranged to transmit the crushing force to the sample material where the crushing force transfers energy to the sample material of at least about 10 Joules.

23. The sample holder of claim 18, wherein the first and second layers have a thickness of between about 0.0005 and 0.0005 inches.

24. The sample holder of claim 18, wherein the first vessel is sealed in a substantially air tight fashion with the first and second layers covering the bottom and top openings, respectively.

25. A sample holder comprising:
a support structure defining a substantially rigid sidewall of a vessel, the support structure defining a bottom opening and a top opening,
a first layer of flexible film attached to the support structure, the first layer of film covering the bottom opening,
a second layer of flexible film attached to the support structure, the second layer covering the top opening,
wherein the first and second layers of film are separated from each other by the sidewall and are arranged to transmit a crushing force exerted on the first and second layers to crush a sample material contained in the vessel, and
wherein the support structure is arranged for use as a standard microscope slide.

26. The holder of claim 25, wherein at least a portion of the sidewall extends from a generally planar body of the support structure.

27. The holder of claim 25, wherein the first and/or second layer is formed of a polymide, a polysulfone, a fluorinated polymer or a liquid crystal polymer.

28. The holder of claim 25, wherein the first and second layers are arranged to transmit the crushing force to the sample material while at temperatures less than about −40 degrees C.

29. The holder of claim 25, wherein the first and second layers are arranged to transmit the crushing force to the sample material at temperatures less than about −40 degrees C. without cracking, tearing, or ripping when exposed to the crushing force.

30. The holder of claim 25, wherein the first and second layers are arranged to transmit the crushing force to the sample material where the crushing force transfers energy to the sample material of at least about 10 Joules.

31. The holder of claim 25, wherein the first and second layers have a thickness of between about 0.0005 and 0.005 inches.

32. The holder of claim 25, wherein the vessel is sealed in a substantially air tight fashion with the first and second layers covering the bottom and top openings, respectively.

* * * * *

UNITED STATES PATENT AND TRADEMARK OFFICE
CERTIFICATE OF CORRECTION

PATENT NO.        : 8,709,359 B2
APPLICATION NO.   : 12/984919
DATED             : April 29, 2014
INVENTOR(S)       : James A. Laugharn, Jr.

It is certified that error appears in the above-identified patent and that said Letters Patent is hereby corrected as shown below:

In the Claims

At column 11, claim 1, line 62, delete the word "sealing" and replace it with the word -- sealingly --

At column 12, claim 9, line 24, please delete the "." after the "C"

At column 12, claim 11, line 32, after the word "and" delete "0.0005" and replace it with -- 0.005 --

At column 12, claim 18, line 63, please replace the word "cover" with -- covering --

At column 13, claim 21, line 20, please delete the "." after the "C"

At column 13, claim 23, line 28, delete "0.0005" and replace it with -- 0.005 --

At column 14, claim 25, line 22, after the word "opening" delete "," and insert -- ; and --

At column 14, claim 27, line 15, please replace the word "polymide" with -- polyimide --

At column 14, claim 29, line 24, please delete the "." after the "C"

Signed and Sealed this
Twenty-ninth Day of July, 2014

Michelle K. Lee
*Deputy Director of the United States Patent and Trademark Office*